United States Patent
Giladi et al.

(10) Patent No.: US 12,415,083 B2
(45) Date of Patent: Sep. 16, 2025

(54) IMPLANTABLE ARRAYS FOR PROVIDING TUMOR TREATING FIELDS

(71) Applicant: NOVOCURE GMBH, Baar (CH)

(72) Inventors: Moshe Giladi, Haifa (IL); Uri Weinberg, Haifa (IL)

(73) Assignee: Novocure GmbH, Baar (CH)

( * ) Notice: Subject to any disclaimer, the term of this patent is extended or adjusted under 35 U.S.C. 154(b) by 0 days.

(21) Appl. No.: 18/500,598

(22) Filed: Nov. 2, 2023

(65) Prior Publication Data

US 2024/0082593 A1 Mar. 14, 2024

Related U.S. Application Data

(63) Continuation of application No. 17/336,919, filed on Jun. 2, 2021, now Pat. No. 11,839,771.

(Continued)

(51) Int. Cl.
*A61N 1/05* (2006.01)
*A61N 1/04* (2006.01)
(Continued)

(52) U.S. Cl.
CPC .................... *A61N 1/40* (2013.01); *A61N 1/05* (2013.01)

(58) Field of Classification Search
CPC .......... A61N 1/40; A61N 1/05; A61N 1/0529; A61N 1/06; A61B 2018/00285; A61B 2018/147; A61B 5/24; A61B 5/293; A61B 5/6868; A61B 5/291; A61B 5/6882; A61B 5/0031; A61B 2018/00363; A61B 2018/00577; A61B 2562/125; A61B 18/1482; A61B 18/16; A61B 2090/376;
(Continued)

(56) References Cited

U.S. PATENT DOCUMENTS 4,913,164 A * 4/1990 Greene ................. A61N 1/057
607/126
5,904,711 A * 5/1999 Flom ........................ A61N 1/05
607/129

(Continued)

FOREIGN PATENT DOCUMENTS

| WO | 2004030760 | 4/2004 |
| WO | 2005115535 | 12/2005 |
| WO | 2006085150 | 8/2006 |
| WO | 2006131817 | 12/2006 |
| WO | 2011143468 | 11/2011 |

*Primary Examiner* — Carl H Layno
*Assistant Examiner* — Anh-Khoa N Dinh
(74) *Attorney, Agent, or Firm* — Ballard Spahr LLP

(57) ABSTRACT

An apparatus for generating an electric field has a plurality of elongate elements, the plurality of elongate elements including at least a first elongate element and a second elongate element. Each elongate element of the plurality of elongate elements has a proximal end, an opposed distal end and at least one stimulation zone. The plurality of elongate elements are coupled together at their respective proximal ends. The plurality of elongate elements are selectively moveable about and between a retracted position and a deployed position. In the retracted position, the respective distal ends of the first and second elongate elements are spaced by a first distance, and in the deployed position, the respective distal ends of the first and second elongate elements are spaced by a second distance that is greater than the first distance.

20 Claims, 13 Drawing Sheets

Related U.S. Application Data

(60) Provisional application No. 63/033,511, filed on Jun. 2, 2020, provisional application No. 63/033,518, filed on Jun. 2, 2020.

(51) Int. Cl.
*A61N 1/06* (2006.01)
*A61N 1/40* (2006.01)

(58) Field of Classification Search
CPC .... A61B 2090/3966; A61B 2090/3983; A61B 2562/046; A61B 2562/164; A61B 2562/166; A61B 2562/222; A61B 5/263; A61B 5/271; A61B 5/283; A61B 5/686
See application file for complete search history.

(56) References Cited

U.S. PATENT DOCUMENTS

| | | |
|---|---|---|
| 11,337,749 B2 | 5/2022 | DeSimone et al. |
| 2003/0065364 A1* | 4/2003 | Wellman ............ A61B 18/1482 607/5 |
| 2006/0041277 A1* | 2/2006 | Deem ................ A61N 1/36117 607/3 |
| 2012/0071936 A1 | 3/2012 | Pianca et al. |
| 2018/0289954 A1 | 10/2018 | Hebb et al. |
| 2019/0023804 A1* | 1/2019 | Onik .................. C07K 16/2818 |
| 2020/0069364 A1 | 3/2020 | Salahieh |

\* cited by examiner

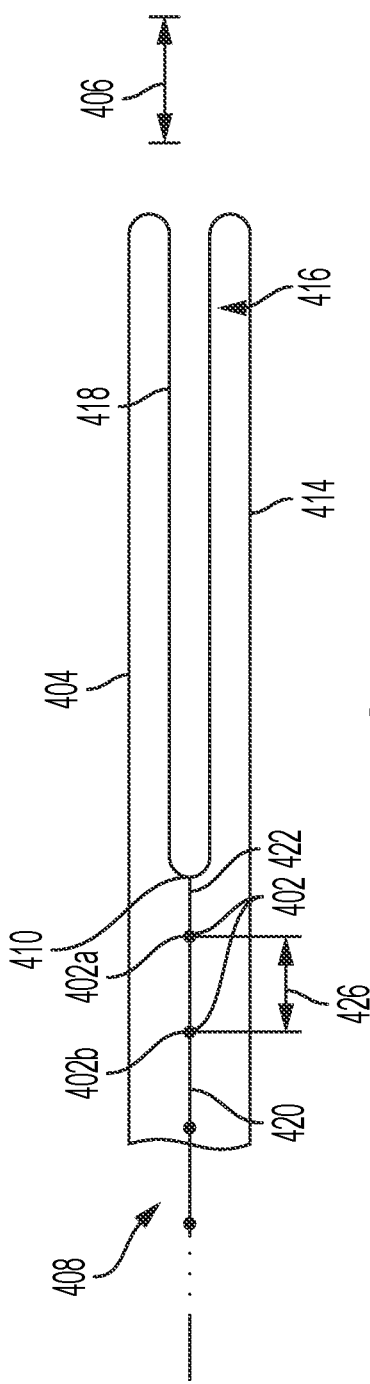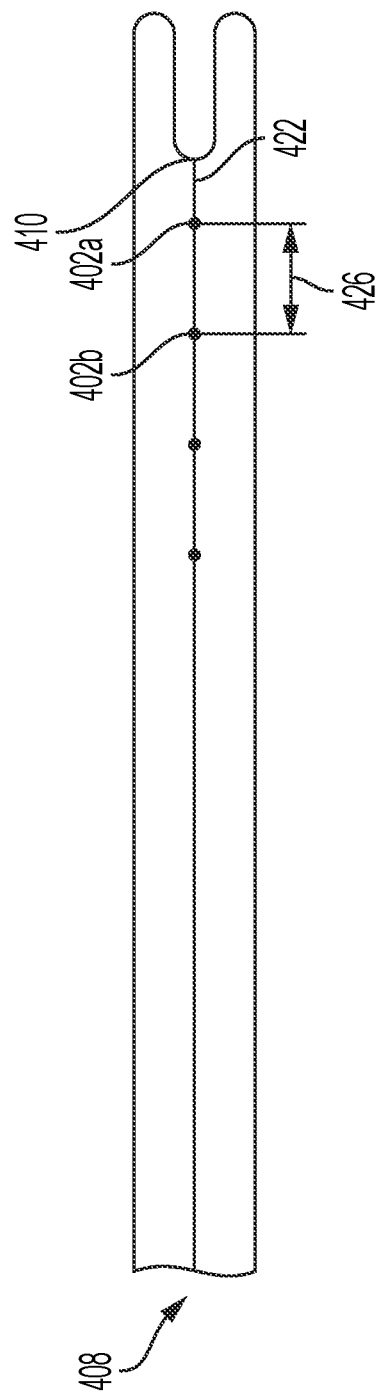

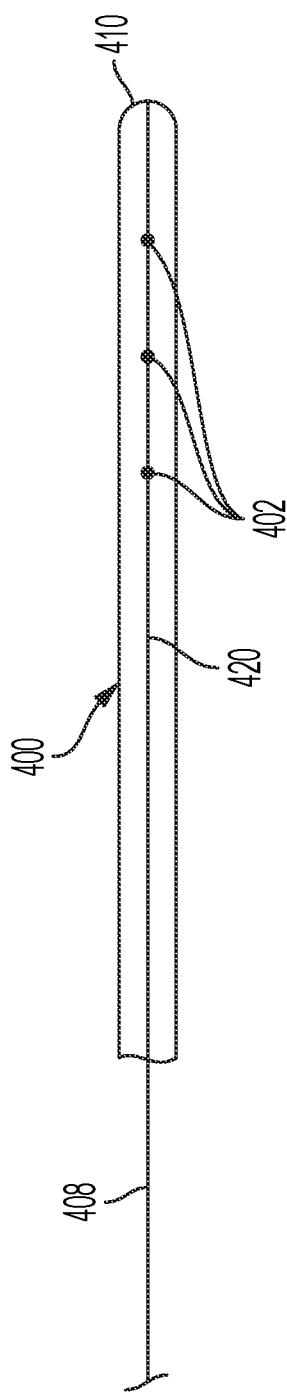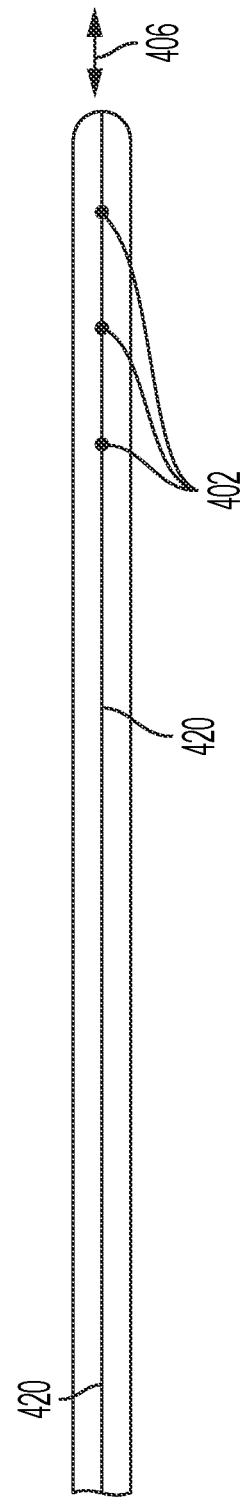
FIG. 6A
FIG. 6B

IMPLANTABLE ARRAYS FOR PROVIDING TUMOR TREATING FIELDS

CROSS-REFERENCE TO RELATED APPLICATIONS

This application is a continuation of U.S. patent application Ser. No. 17/336,919, filed Jun. 2, 2021, now U.S. Pat. No. 11,839,771 B2, which claims priority to and the benefit of the filing date of U.S. Provisional Patent Application No. 63/033,511, filed Jun. 2, 2020, and U.S. Provisional Patent Application No. 63/033,518, filed Jun. 2, 2020, each of which is incorporated herein by reference in its entirety.

FIELD

This application relates generally to apparatuses and methods for providing tumor treating fields and, in particular, for apparatuses and methods for implanting electrodes within a patient for providing tumor treating fields.

BACKGROUND

Tumor Treating Fields, or TTFields, are low intensity (e.g., 1-3 V/cm) alternating electrical fields within the intermediate frequency range (100-300 kHz). This non-invasive treatment targets solid tumors and is described in U.S. Pat. No. 7,565,205, which is incorporated herein by reference in its entirety. TTFields disrupt cell division through physical interactions with key molecules during mitosis. TTFields therapy is an approved mono-treatment for recurrent glioblastoma, and an approved combination therapy with chemotherapy for newly diagnosed patients. Conventionally, these electrical fields are induced non-invasively by transducer arrays (i.e., arrays of electrodes) placed directly on the patient's scalp. TTFields also appear to be beneficial for treating tumors in other parts of the body.

SUMMARY

Described herein, in various aspects, is an apparatus for generating an electric field. The apparatus can have plurality of elongate elements. The plurality of elongate elements can have at least a first elongate element and a second elongate element. Each elongate element of the plurality of elongate elements can have a proximal end, an opposed distal end, and at least one stimulation zone. The plurality of elongate elements can be coupled together at their respective proximal ends. The plurality of elongate elements can be selectively moveable about and between a retracted position and a deployed position. In the retracted position, the respective distal ends of the first and second elongate elements can be spaced by a first distance. In the deployed position, the respective distal ends of the first and second elongate elements can be spaced by a second distance that is greater than the first distance.

In other aspects, described herein is an apparatus having a bladder and a plurality of stimulation zones coupled to the bladder. The plurality of stimulation zones can include a first stimulation zone and a second stimulation zone. The plurality of stimulation zones can be configured to produce an electric field. Inflation of the bladder can cause the plurality of stimulation zones to deploy from a retracted configuration to a deployed configuration. When the plurality of stimulation zones are in the retracted configuration, the first and second stimulation zones are spaced by a first distance. When the plurality of stimulation zones are in the deployed configuration, the first and second stimulation zones are spaced by a second distance that is greater than the first distance.

In other aspects, described herein is an apparatus having an inflatable body and a plurality of stimulation zones coupled to the inflatable body. The plurality of stimulation zones can be configured to produce an electric field. Inflation of the body can cause elongation of the body along a longitudinal axis of the body.

In other aspects, described herein is an apparatus having a first body, a plurality of stimulation zones disposed along the first body, a second body, and an actuator. The first body can be telescopically coupled to the second body so that the first body is slidable with respect to the second body along a longitudinal axis of the apparatus. The plurality of stimulation zones can be configured to produce an electric field. The actuator can be configured to slide the first body with respect to the second body.

In other aspects, described herein is a system having a guide and an electric field-generating assembly. The guide can include an inflatable body having a longitudinal axis. The electric field-generating assembly can be configured for receipt within the inflatable body. The electric field-generating assembly can include a cable having a length and a plurality of stimulation zones disposed along the length of the cable. The plurality of stimulation zones are configured to produce an electric field.

Methods of using the disclosed apparatuses and systems are also described.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

These and other features of the preferred embodiments of the invention will become more apparent in the detailed description in which reference is made to the appended drawings wherein:

FIG. 5A is a schematic side view of an inflatable implantable tumor treating field apparatus as disclosed herein, wherein the apparatus is in the deflated configuration. FIG. 5B is a schematic side view of the implantable tumor treating field apparatus as in FIG. 5A, wherein the apparatus is in the inflated configuration.

FIG. 6A is a schematic side view of an inflatable implantable tumor treating field apparatus as disclosed herein, wherein the apparatus is in the deflated configuration. FIG. 6B is a schematic side view of the implantable tumor treating field apparatus as in FIG. 6A, wherein the apparatus is in the inflated configuration.

DETAILED DESCRIPTION

Figure 1A:
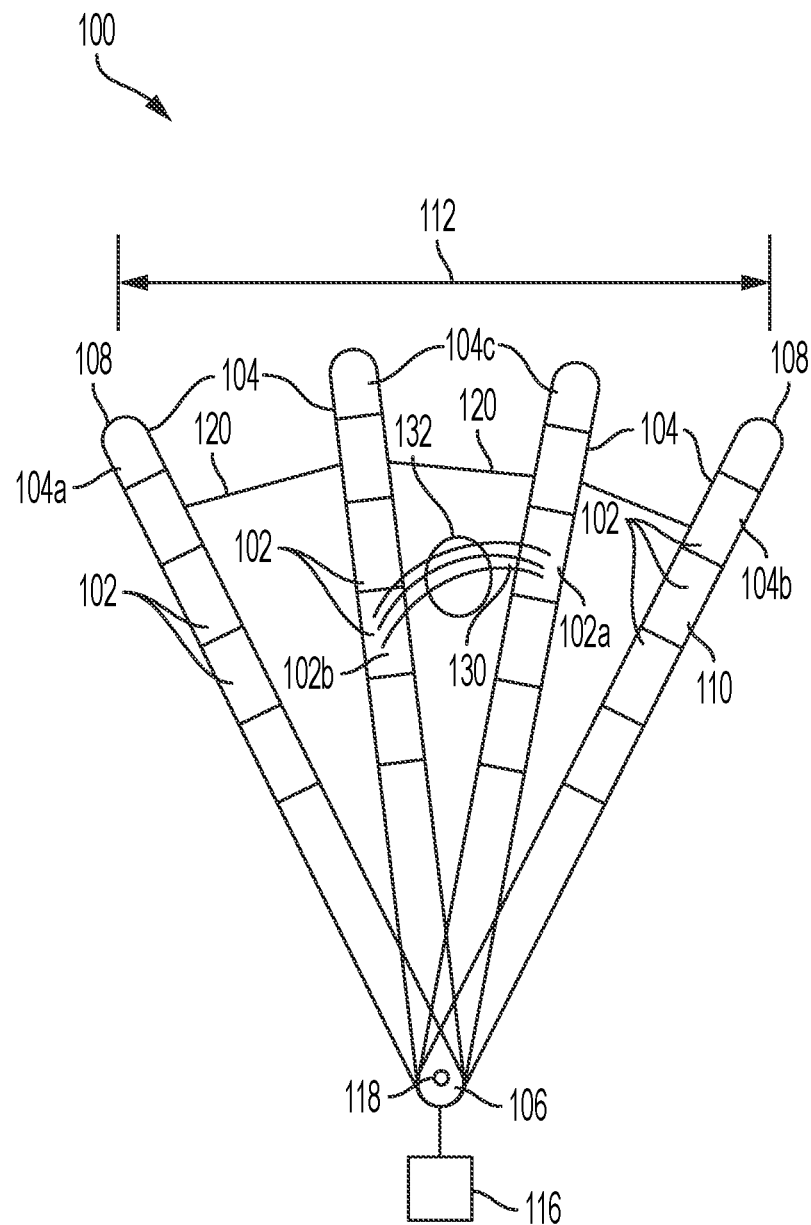
FIG. 1A is a schematic side view of an implantable tumor treating field apparatus as disclosed herein, wherein the implantable tumor treating field apparatus comprises elongate elements that are in a deployed configuration.

The disclosed system and method may be understood more readily by reference to the following detailed description of particular embodiments and the examples included therein and to the Figures and their previous and following description.

It is to be understood that the terminology used herein is for the purpose of describing particular embodiments only and is not intended to limit the scope of the present invention which will be limited only by the appended claims.

It must be noted that as used herein and in the appended claims, the singular forms "a", "an," and "the" include plural references unless the context clearly dictates otherwise. Thus, for example, reference to "an electrode" includes one or more of such electrodes, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Optionally, in some aspects, when values are approximated by use of the antecedents "about," "substantially," or "generally," it is contemplated that values within up to 15%, up to 10%, up to 5%, or up to 1% (above or below) of the particularly stated value or characteristic can be included within the scope of those aspects.

Unless defined otherwise, all technical and scientific terms used herein have the same meanings as commonly understood by one of skill in the art to which the disclosed apparatus, system, and method belong. Although any apparatus, systems, and methods and materials similar or equivalent to those described herein can be used in the practice or testing of the present apparatus, system, and method, the particularly useful methods, devices, systems, and materials are as described.

As used herein, the term "patient" refers to a human or animal subject who is in need of treatment using the disclosed systems and devices.

As used herein, the term "electrode" refers to any structure that permits generation of an electric potential, electric current, or electrical field as further disclosed herein. Optionally, an electrode can comprise a transducer. Optionally, an electrode can comprise a non-insulated portion of a conductive element. In the description herein, any description of a "transducer" or "transducer array" can be applied to an "electrode," and any description of an "electrode" can be applied to a "transducer" or "transducer array."

As used herein, the term "stimulation zone" refers to any structural arrangement that permits generation of an electrical field as further disclosed herein. Optionally, a stimulation zone can comprise an electrode and/or a transducer. Optionally, a stimulation zone can comprise a non-insulated portion of a conductive element.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Tumor-Treating Fields (TTFields), also referred to herein as alternating electric fields, are established as an anti-mitotic cancer treatment modality because they interfere with proper micro-tubule assembly during metaphase and eventually destroy the cells during telophase and cytokinesis. The efficacy increases with increasing field strength and the optimal frequency is cancer cell line dependent with 200 kHz being the frequency for which inhibition of glioma cells growth caused by TTFields is highest. For cancer treatment, non-invasive devices were developed with capacitively coupled transducers that are placed directly at the skin region close to the tumor. For patients with Glioblastoma Multiforme (GBM), the most common primary, malignant brain tumor in humans, the system for delivering TTFields therapy is called the OP TUNE™ system (Novocure Ltd.).

Because the effect of TTFields is directional with cells dividing parallel to the field affected more than cells dividing in other directions, and because cells divide in all directions, TTFields are typically delivered through two pairs of transducer arrays that generate perpendicular fields within the treated tumor. More specifically, for the OPTUNE system, one pair of electrodes is located to the left and right (LR) of the tumor, and the other pair of electrodes is located anterior and posterior (AP) to the tumor. Cycling the field between these two directions (i.e., LR and AP) ensures that a maximal range of cell orientations is targeted.

Figure 11:
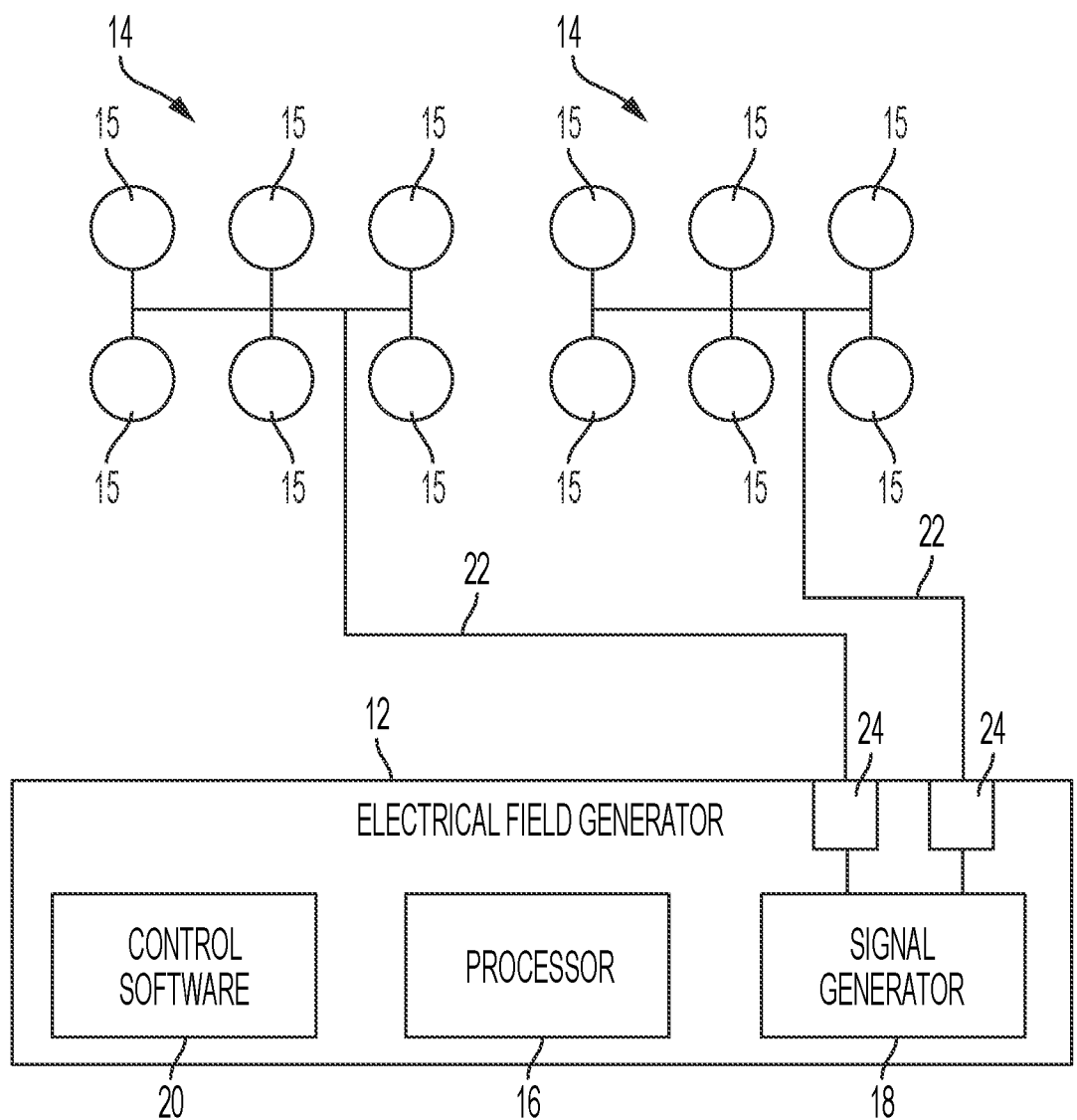
FIG. 11 is a system for delivering tumor treating fields using the implantable apparatuses and systems as disclosed herein.

FIG. 11 shows an example apparatus 10 for electrotherapeutic treatment as disclosed herein. Generally, the apparatus 10 may be a portable, battery or power supply operated device that produces alternating electrical fields within the body by means of stimulation zones as disclosed herein (e.g., transducer arrays or electrodes). The apparatus 10 may comprise an electrical field generator 12 and one or more stimulation zones (shown in this exemplary configuration as transducer arrays 14). The apparatus 10 may be configured to generate tumor treating fields (TTFields) (e.g., at 150 kHz) via the electrical field generator 12 and deliver the TTFields to an area of the body through the stimulation zones (e.g., one or more transducer arrays 14 or electrodes). The electrical field generator 12 may be powered by a battery and/or power supply.

As shown in FIG. 11, each transducer array 14 can comprise a plurality of electrodes or transducers 15. In exemplary aspects, the transducers 15 can capacitively couple an AC signal into a subject's body. In further aspects, the transducers 15 can comprise a layer of conductive material, such as a layer of at least one metal (e.g., stainless steel, gold, and/or copper). Additionally, or alternatively, it is contemplated that the transducers 15 can comprise a layer of conductive hydrogel. Exemplary transducers 15 can further comprise ceramic discs, such as described in U.S. Pat. No. 8,715,203, which is incorporated herein by reference. In additional or alternative aspects, it is contemplated that the transducers 15 can comprise polymer insulating layers and/or other insulating material. Optionally, in exemplary aspects, it is contemplated that one or more of the various layers of the transducers 15 can be flexible and of minimal thickness, thereby allowing easier advancement of the transducer arrays 14 within the body of a subject as further disclosed herein.

The electrical field generator 12 may comprise a processor 16 in communication with a signal generator 18. The electrical field generator 12 may comprise control software 20 configured for controlling the performance of the processor 16 and the signal generator 18.

The signal generator 18 may generate one or more electric signals in the shape of waveforms or trains of pulses. The signal generator 18 may be configured to generate an alternating voltage waveform at frequencies in the range from about 50 KHz to about 500 KHz (preferably from about 100 KHz to about 300 KHz) (e.g., the TTFields). The voltages are such that the electrical field intensity in tissue to be treated is typically in the range of about 0.1 V/cm to about 10 V/cm.

One or more outputs 24 of the electrical field generator 12 may be coupled to one or more conductive leads 22 that are attached at one end thereof to the signal generator 18. The opposite ends of the conductive leads 22 are connected to the one or more stimulation zones (e.g., transducer arrays 14) that are activated by the electric signals (e.g., waveforms). The conductive leads 22 may comprise standard isolated conductors with a flexible metal shield and may be grounded to prevent the spread of the electrical field generated by the conductive leads 22. The one or more outputs 24 may be operated sequentially. Output parameters of the signal generator 18 may comprise, for example, an intensity of the field, a frequency of the waves (e.g., treatment frequency), and a maximum allowable temperature of the one or more stimulation zones (e.g., transducer arrays 14). The output parameters may be set and/or determined by the control software 20 in conjunction with the processor 106. After determining a desired (e.g., optimal) treatment frequency, the control software 20 may cause the processor 16 to send a control signal to the signal generator 18 that causes the signal generator 18 to output the desired treatment frequency to the one or more stimulation zones (e.g., transducer arrays 14).

The one or more stimulation zones (e.g., transducer arrays 14) may be configured in a variety of shapes and positions so as to generate an electrical field of the desired configuration, direction and intensity at a target volume so as to focus treatment. Optionally, the one or more stimulation zones (e.g., transducer arrays 14) may be configured to deliver two perpendicular field directions through the volume of interest.

Although transducers are conventionally positioned externally on the patient, the present disclosure recognizes that there are benefits to positioning electrodes or transducers within the body of the patient to provide localized electric fields at the site of the tumor. As further described herein, after the electrodes or transducer arrays 14 are selectively positioned within the body of a subject (e.g., in proximity to a target site such as a tumor), an AC voltage can be applied using the electrodes or transducer arrays. A layer of conductive material within the transducers can act as a capacitor's plate, and an insulating layer comprising a polymer, a ceramic material, and/or a coating can act as a capacitor's insulating layer, thereby allowing an AC electric field to be capacitively coupled through the electrodes or transducer arrays 14 into the body of the subject.

Figure 1B:
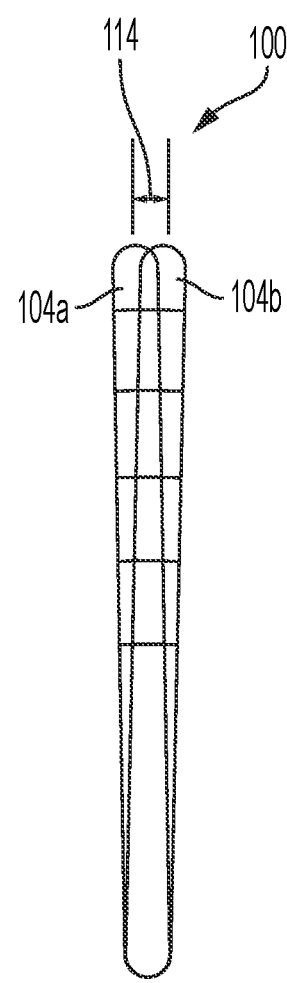
FIG. 1B is a schematic side view of the implantable tumor treating field apparatus as in FIG. 1A, with the elongate elements in a retracted configuration.

Disclosed herein, in various aspects and with reference to FIGS. 1A-1B, is an implantable tumor treating field (TTField) apparatus 100. In some aspects, the apparatus 100 can comprise a plurality of elongate elements 104, each elongate element 104 having a proximal end 106 and a distal end 108. The plurality of elongate elements 104 can be coupled together at their respective proximal ends 106. The plurality of elongate elements 104 can comprise at least a first elongate element 104a and a second elongate element 104b.

The plurality of elongate elements 104 can be selectively movable about and between a retracted position (FIG. 1B) and a deployed position (FIG. 1A). In the deployed position, the respective distal ends 108 of the first and second elongate elements 104a, 104b can be spaced by a first distance 112. In the retracted position, the respective distal ends 108 of the first and second elongate elements 104a, 104b can be spaced by a second distance 114 that is less than the first distance 112. Exemplary materials for the elongate elements 104 include stainless steel, titanium alloy, cobalt chrome alloy, tantalum, or biocompatible polymer materials. In exemplary aspects, it is contemplated that the elongate elements 104 can comprise a conductive material. For example, in some optional aspects, the elongate elements 104 can comprise conductive thermoplastic materials, which can optionally comprise conductive additives.

In some aspects, the elongate elements can be arranged back-to-back (e.g., in the manner of slats on a hand fan) so that, when in the retracted position, the distal ends of the first and second elements can be aligned in a first transverse dimension (e.g., into the page), and the distal ends can be separated only by the thicknesses of the elongate elements in said first transverse dimension. Thus, for the view shown in FIG. 1B, in some optional aspects, the first elongate element 104a can entirely cover the second elongate element 104b. In exemplary aspects, the elongate elements 104 can be pivotably coupled together by a hinge 118 that extends in the first transverse dimension. Optionally, in these aspects, the hinge 118 can comprise conductive material.

In some aspects, the apparatus can comprise an actuator 116 that is configured to pivot the first and second elongate elements 104a, 104b about the hinge 118. The actuator 116 can be, for example, a dial actuator (optionally, a dial actuator coupled to a rotation knob as is known in the art) or other actuator commonly known and used in laparoscopic procedures, such as those used in laparoscopic fan retractors. Optionally, in some exemplary aspects, the actuator 116 can comprise a shaft (not shown) and a catch or lock (not shown) that is coupled to a distal end of the shaft and configured to selectively engage and disengage the proximal ends 106 of the elongate elements 104, with engagement between the catch/lock and the elongate elements restricting or preventing outward pivotal movement and disengagement permitting outward pivotal movement. It is contemplated that the catch/lock can be selectively engaged with or disengaged from the proximal ends 106 of the elongate elements 104 in response to user-actuation of a button that is mechanically coupled to the catch/lock such that depression of the button causes a release of the catch/lock from engagement with the elongate elements and release of the button causes the catch/lock to return to a locking position. Optionally, the actuator 116 can comprise a spring or other biasing element that biases at least one of the first elongate element 104a or the second elongate element 104b toward outward pivotal movement such that upon disengagement of the catch/lock, the elongate elements pivot outwardly. Additionally, or alternatively, in further aspects, the actuator 116 can comprise an actuation cable (not shown) that mechanically couples to at least one of the first elongate element 104a or the second elongate element 104b, and a tension applied to the actuation cable can cause the plurality of elongate elements 104 to move to the deployed position. Although described herein as an "actuation cable," it is contemplated that any elongate element permitting application of tension to the elongate elements through the elongate element (e.g., a cable, a rod, and the like) can be used for this purpose. Additionally, or alternatively, it is contemplated that the actuator 116 can comprise a screw or other rotatable component that is coupled to one of the first or second elongate elements 104a, 104b and configured to drive movement of the elongate element about the rotational axis of the screw. In these aspects, it is contemplated that the actuator 116 can further comprise a screwdriver or other rotational actuator that is configured to drive rotation of the screw (or other rotatable component) to drive rotational movement of the elongate element to deploy the elongate elements. Additionally, or alternatively, in still further aspects, the actuator 116 can comprise first and second actuators that are respectively coupled to the first and second elongate elements 104a, 104b. For example, in some aspects, it is contemplated that a first rod can be coupled to the first elongate element 104a, while a second rod can be coupled to the second elongate element 104b. In these aspects, it is contemplated that the first and second rods can be coupled to the first and second elongate elements such that movement of the proximal ends of the rods (e.g., rotational movement or axial movement) causes a corresponding translation of the distal ends of the rods, which effects pivotal movement of the elongate elements.

In some optional aspects, the plurality of elongate elements 104 can further comprise one or more intermediate elongate elements 104c. The intermediate elongate elements 104c can be positioned between, and coupled to, the first and second elongate elements 104a, 104b. For example, webbings or support cables 120 can extend between, and couple to, adjacent elongate elements 104. In this way, as the first and second elongate elements are moved from the retracted position to the second position, the webbings or support cables 120 can position the intermediate elongate elements 104c at select positions (e.g., spaced positions) between the first and second elongate elements 104a, 104b. Essentially, the first and second elongate elements 104a, 104b can be fanned out, thereby spacing the intermediate elongate elements 104c therebetween. In exemplary aspects, when the elongate elements are in a fully deployed position, it is contemplated that the webbings or support cables 120 can apply sufficient tension to maintain the relative positions of the elongate elements. In these aspects, it is contemplated that the webbings or support cables 120 can comprise flexible materials that do not restrict full retraction of the elongate elements. For example, it is contemplated that the webbings or support cables 120 can flex or be deformed to be accommodated between overlapping portions of adjacent elongate elements as the elongate elements are retracted.

The elongate elements 104 can each comprise one or more stimulation zones 102, which can optionally be provided as respective locations of one or more transducers or electrodes. In some optional aspects, the stimulation zones can be portions of the elongate elements. For example, optionally, the elongate elements 104 can be generally covered in insulating material ("insulation"), and the stimulation zones 102 can be portions of the elongate elements without insulation. Exemplary insulating materials include, without limitation, polyvinylidene fluoride (PVDF), low-density polyethylene (LDPE), high-density polyethylene (HDPE), fluorinated ethylene propylene (FEP), polyvinyl chloride (PVC), polyolefin-based co-polymers, ethylene acrylic acid-based copolymers, polytetrafluoroethylene (PTFE), or combinations thereof. In further aspects, the simulation zones 102 can be coupled to the elongate elements 104. The stimulation zones 102 can optionally be ring-shaped.

As disclosed herein, each stimulation zone can comprise, for example, an electrode 110 or a transducer array. The electrodes 110 can be, for example, conductive or capacitive electrodes. The electrodes can optionally comprise a ceramic material. In further aspects, the electrodes can comprise a metal (e.g., gold, platinum, copper, stainless steel, etc.) or a non-metal (e.g., a polymer such as, for example, polytetrafluoroethylene (ePTFE), polyethylene-co-tetrafluoroethene (ETFE), polyurethanes, silicones, etc.). Optionally, the electrodes can be flexible or rigid. The size and shape of each electrode can be selected based on the desired field produced and the constraints that the respective apparatus provides.

Optionally, each of the stimulation zones can be coupled to a respective electrical lead so that TTFields can be generated between any two select stimulation zones. Accordingly, it is contemplated that each stimulation zone 102 of the plurality of stimulation zones 102 for each elongate element 104 can be independently activated to provide electric fields 130 between itself and any other stimulation zone 102. For example, a first stimulation zone 102a and a second stimulation zone 102b can be activated to generate electric fields therebetween. Thus, each stimulation zones 102 on any elongate element 104 can be independent of the other stimulation zones 102 on the same elongate element 104. Optionally, the elongate elements can comprise a bundle of electrical leads with exposed portions (without insulation) that function as stimulation zones as disclosed herein.

In some aspects, the implantable TTField apparatus 100 can have an electrical lead 22 (FIG. 11) coupled thereto and extending therefrom. The electrical lead can comprise a plurality of conductors, with each conductor being in communication with a respective stimulation zone 102. In some optional aspects, the electrical lead 22 can have a sufficient rigidity so that a pushing force at the end of the electrical lead opposite the TTField apparatus can effect movement of the TTField apparatus within the body of the patient.

Figure 2A:
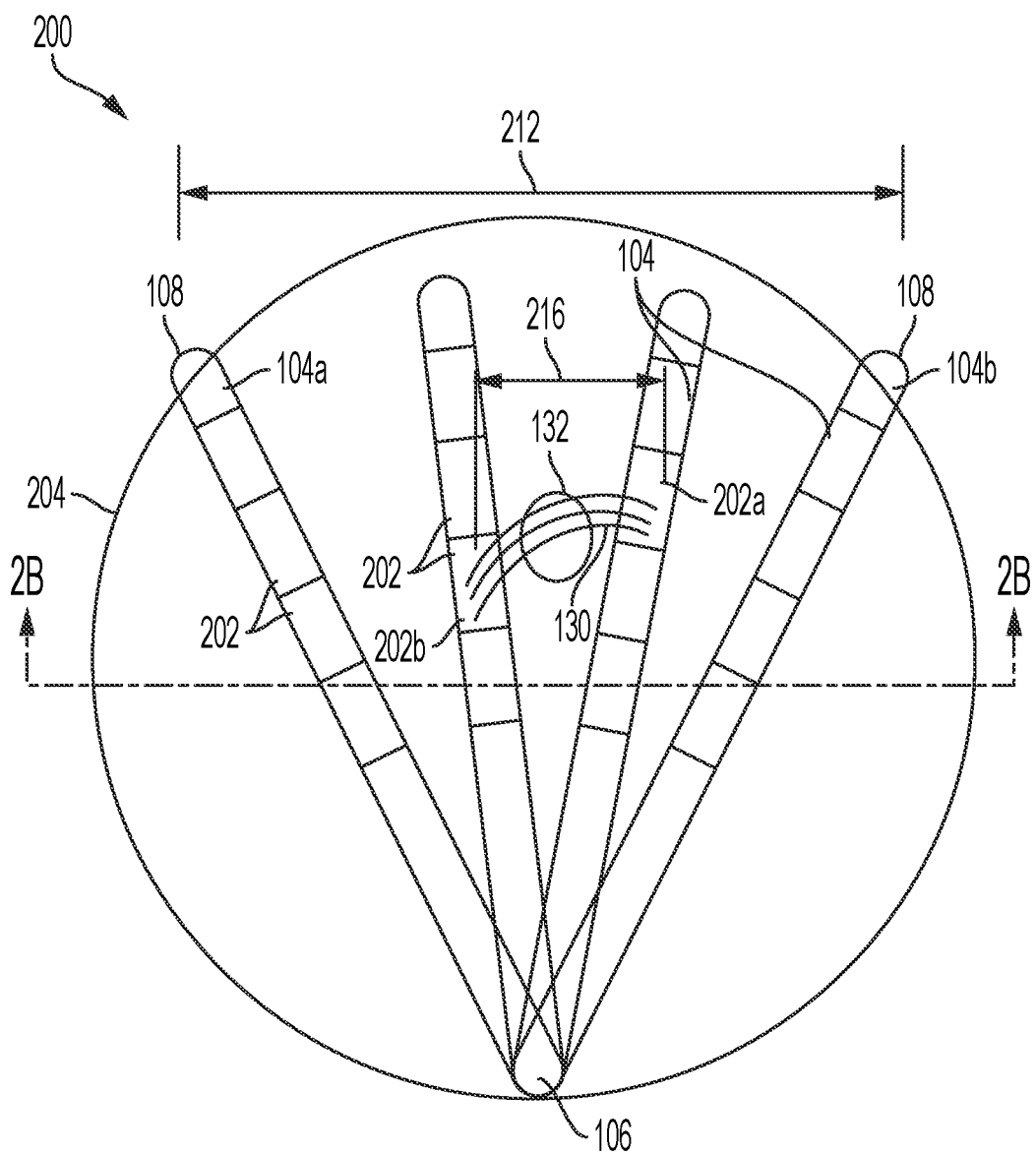
FIG. 2A is a schematic side view of an implantable tumor treating field apparatus as disclosed herein, wherein the implantable tumor treating field apparatus comprises elongate elements that are in a deployed configuration.
Figure 2B:
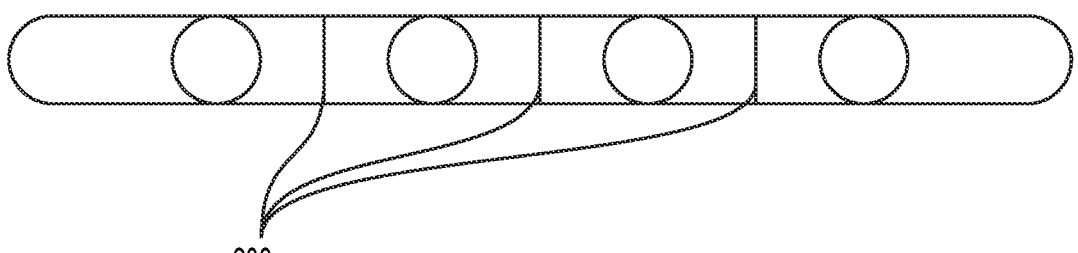
FIG. 2B is a cross section of the implantable tumor treating field apparatus as in FIG. 2A, taken at line 2B-2B.

Referring to FIGS. 2A and 2B, in further aspects, an implantable TTField apparatus 200 can comprise a bladder 204. A plurality of stimulation zones 202 can be coupled to the bladder. In some aspects, the stimulation zones 202 can be portions of the bladder, and the stimulation zones 202 can be coupled to the bladder via integral formation. For example, the bladder 204 can be a conductor (i.e., comprising a conductive material) that is covered or generally covered in insulation (i.e., non-conductive material), and non-insulated portions of the bladder 204 can act as stimulation zones 202. In some optional aspects, it is contemplated that the bladder can comprise an electrically conductive mesh, conductive nanosheet(s), electrically conductive rubber (e.g., silicone rubber), or a printed conductive layer (with conductive ink).

In further aspects, the bladder 204 can be a non-conductive material, such as, for example, a ceramic or non-conductive polymer, and the stimulation zones 202 can be disposed within, or coupled to an outer surface of, the bladder 204. Optionally, in exemplary aspects, all or some of the stimulation zones 202 can comprise one or more transducers.

The bladder can be inflated to deploy the stimulation zones 202 from a retracted configuration (FIG. 2C) to a deployed configuration (FIG. 2A). The plurality of stimulation zones 202 can be comprise at least a first stimulation zone 202a and a second stimulation zone 202b. When in the retracted configuration, the first and second stimulation zones 202a, 202b can be spaced by a first distance 214. When in the deployed configuration, the first and second stimulation zones 202a, 202b can be spaced by a second distance 216 that is greater than the first distance 214. Optionally, the implantable TTField apparatus 200 can comprise a frame 206 that can be configured to support the bladder and determine the shape of the bladder when the bladder is inflated. For example, the frame can comprise a plurality of webbings 208 that are secured to and extend between portions (e.g., opposing portions) of the bladder so that the webbings restrict expansion of the bladder between the portions of the bladder beyond a select distance. Optionally, the frame can comprise flexible material. Alternatively, the frame can comprise rigid but lightweight materials, such as medical grade metallic or plastic materials.

Figure 2C:
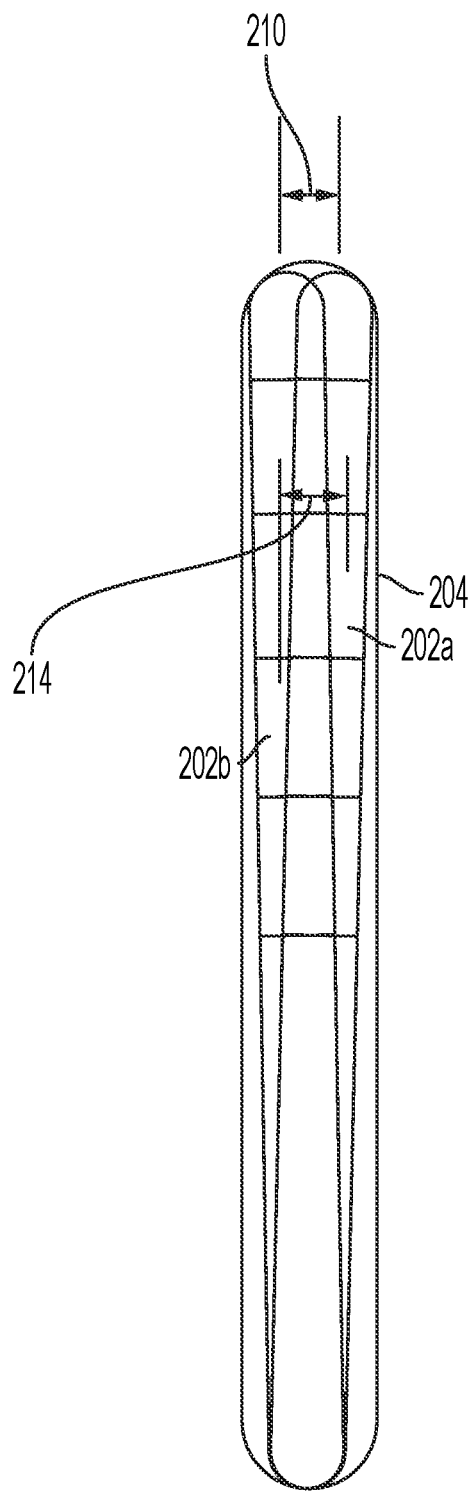
FIG. 2C is a schematic side view of the implantable tumor treating field apparatus as in FIG. 2A, with the elongate elements in a retracted configuration.

In some optional aspects, the stimulation zones 202 can be disposed on a plurality of elongate elements 104. The elongate elements 104 can be each have a proximal end 106 and a distal end 108. The plurality of elongate elements 104 can comprise at least a first elongate element 104a and a second elongate element 104b. The plurality of elongate elements 104 can optionally be coupled together at their respective proximal ends 106 (e.g., via a hinge). The plurality of elongate elements 104 can be coupled to the bladder 204 so that they are deployable via inflation/deflation of the bladder between a retracted position and a deployed position. In the retracted position (FIG. 2C), the respective distal ends 108 of the first and second elongate elements 104a, 104b can be spaced by a third distance 210. When in the deployed position (FIG. 2A), the respective distal ends 108 of the first and second elongate elements 104a, 104b can be spaced by a fourth distance 212 that is greater than the third distance. One or more intermediate elongate elements 104c can be positioned between, and coupled to, the first and second elongate elements 104a, 104b. Thus, whereas the elongate elements 104 depicted in FIGS. 1A-1B are deployed by an actuator (e.g., a mechanical actuator) that directly effects movement of the elongate elements, the elongate elements 104 depicted in FIGS. 2A-2C are deployed by inflation of the bladder to which the elongate elements are coupled.

Figure 3:
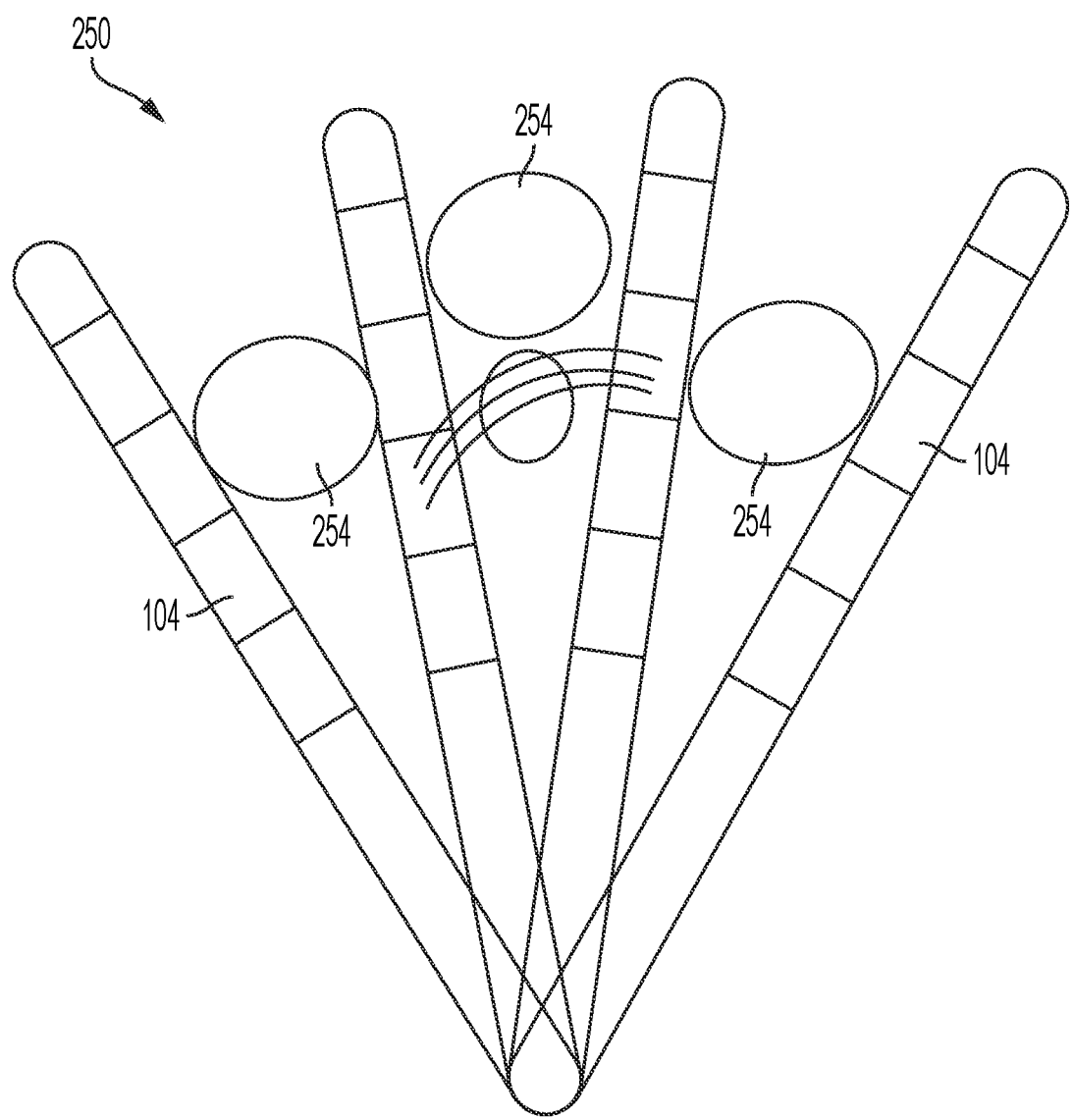
FIG. 3 is a schematic side view of an implantable tumor treating field apparatus as disclosed herein, wherein the implantable tumor treating field apparatus comprises elongate elements that are in a deployed configuration.

Referring to FIG. 3, in some optional aspects, a implantable TTField apparatus 250 can comprise a plurality of bladders 254 (or a single bladder comprising a plurality of inflatable zones) disposed between adjacent elongate elements 104. Inflation of the plurality of bladders 254 can bias the adjacent elongate elements 104 away from each other, thereby deploying the stimulation zones from a retracted configuration to a deployed configuration. In some optional aspects, each bladder 254 can be inflated independently in order to select a spacing between elongate elements 104 that are coupled by each bladder 254. Thus, in these aspects, it is contemplated that at least one of the bladders 254 (or inflatable zones) can be fluidly isolated from at least other bladder (or inflatable zone). Optionally, it is contemplated that each bladder 254 (or inflatable zone) can be fluidly isolated from every other bladder (or inflatable zone).

Figure 4A:
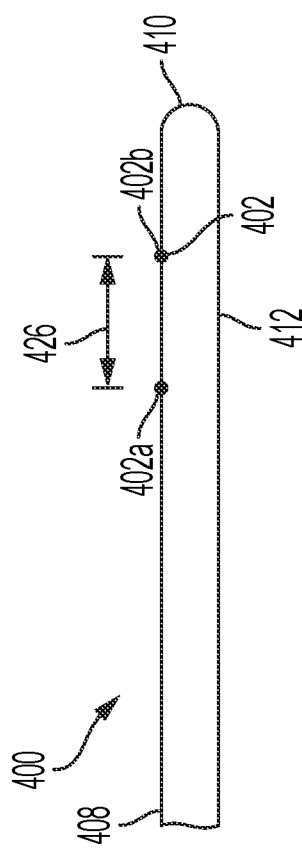
FIG. 4A is a schematic side view of an inflatable implantable tumor treating field apparatus as disclosed herein, wherein the apparatus is in the deflated configuration.
Figure 4B:
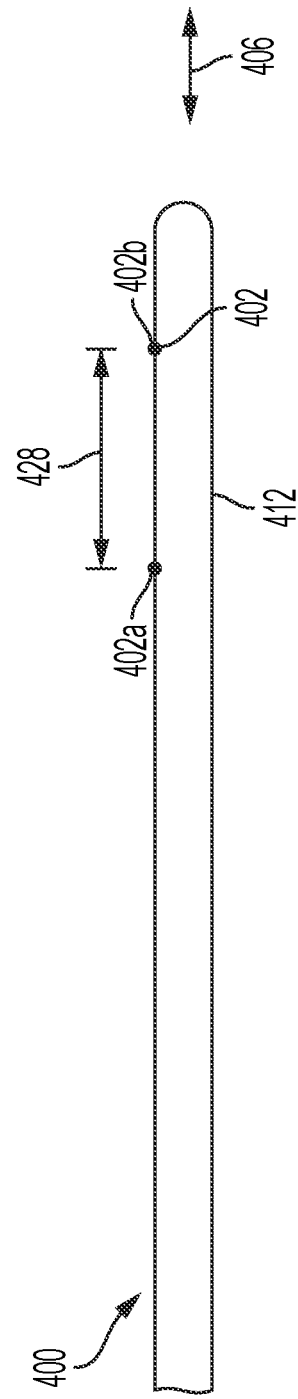
FIG. 4B is a schematic side view of the implantable tumor treating field apparatus as in FIG. 4A, wherein the apparatus is in the inflated configuration.

Referring to FIGS. 4A and 4B, an implantable TTField apparatus 400 can comprise an inflatable body 404 having a longitudinal axis 406. The body 404 can have a proximal end 408 and a distal end 410 that are spaced along the longitudinal axis 406. Inflation of the body can cause elongation of the body along the longitudinal axis. For example, in some aspects, the inflatable body can comprise at least one flexible wall 412. Sufficient pressure within the body can cause the at least one flexible wall 412 to expand to increase the longitudinal length of the body so that the distal end 410 extends in a distal direction (away from the proximal end 408), while the proximal end stays in the same position along the longitudinal axis 406. Thus, after inflation, the distal end 410 can be positioned distally relative to the axial location of the distal end prior to inflation. Optionally, the flexible walls can be elastic membranes that stretch. Additionally, or alternatively, the flexible walls can comprise accordion folds to permit expansion and retraction.

Referring to FIGS. 5A and 5B, in further optional aspects, prior to inflation, the body 404 can be folded in on itself so that a first portion 414 of the body 404 defines an interior space 416, and a second portion 418 (e.g., a distal portion) of the body 404 is folded inwardly (e.g., in a proximal direction) to be received within the interior space 416. The first and second portions 414, 418 of the body can cooperate to define the length of the body 404. The second portion 418 can comprise the distal end 410 of the body 404. As the body is inflated, the body can gradually unfold, thereby pushing the distal end 410 away from the proximal end 408. In still further aspects, the body 404 can be folded within itself three or more times so that at least a third portion of the body is within an interior space defined by the second portion of the body.

As shown in FIGS. 4A-5B, the TTField apparatus 400 can comprise a plurality of stimulation zones 402 coupled to the body 404. The plurality of stimulation zones 402 can comprise a first stimulation zone 402a and a second stimulation zone 402b. In some optional aspects, the stimulation zones 402 can be a portion of the inflatable body 404. For example, the body 404 can be a conductor that is generally covered in insulation, and non-insulated portions of the body 404 can act as stimulation zones 402. In further aspects, the stimulation zones 402 can be separate components that are coupled to the body 404 (e.g., to an outside of the body or an inside of the body). For example, referring to FIGS. 5A-5B and 6A-6B, the stimulation zones 402 can be disposed on a cable 420. A distal end 422 of the cable 420 can be coupled to the distal end 410 of the body 404. In exemplary aspects, it is contemplated that the cable 420 can be secured to the body 404 prior to positioning of the TTField apparatus 400 within the body of the patient. Thus, distal movement of the distal end 410 of the body 404 (in response to inflation) can cause distal movement of the distal end 422 of the cable, thereby drawing the cable 420, and, thus, the stimulation zones 402 outward (away from the proximal end 408). Optionally, the cable 420 can comprise the electrical leads that couple to the respective stimulation zones. Optionally, in exemplary aspects, all or some of the stimulation zones 402 can comprise one or more transducers.

In some aspects, and as shown in FIGS. 4A and 4B, prior to inflation of the inflatable body, the first stimulation zone 402a can be spaced from the second stimulation zone 402b by a first distance 426. Upon inflation of the body 404, the first stimulation zone 402a can be spaced from the second stimulation zone 402b by a second distance 428 that is greater than the first distance 426. Additionally, it is contemplated that the axial distance between each respective stimulation zone and the proximal end 408 of the body 404 can increase in response to inflation. In some further aspects, and as shown in FIGS. 5A and 5B, prior to inflation of the inflatable body, the first stimulation zone 402a can be spaced from the second stimulation zone 402b by a first distance 426. Upon inflation of the body 404, the first stimulation zone 402a can remain spaced from the second conductive zone 402b by the first distance 426. However, when the proximal end 408 of the body 404 remains in a fixed position relative to the longitudinal axis, it is understood that the axial distance between each respective stimulation zone and the proximal end of the body will increase in response to inflation. The same characteristics that apply to the embodiment depicted in FIGS. 5A-5B can also apply to the embodiment depicted in FIGS. 6A-6B.

Figure 7:
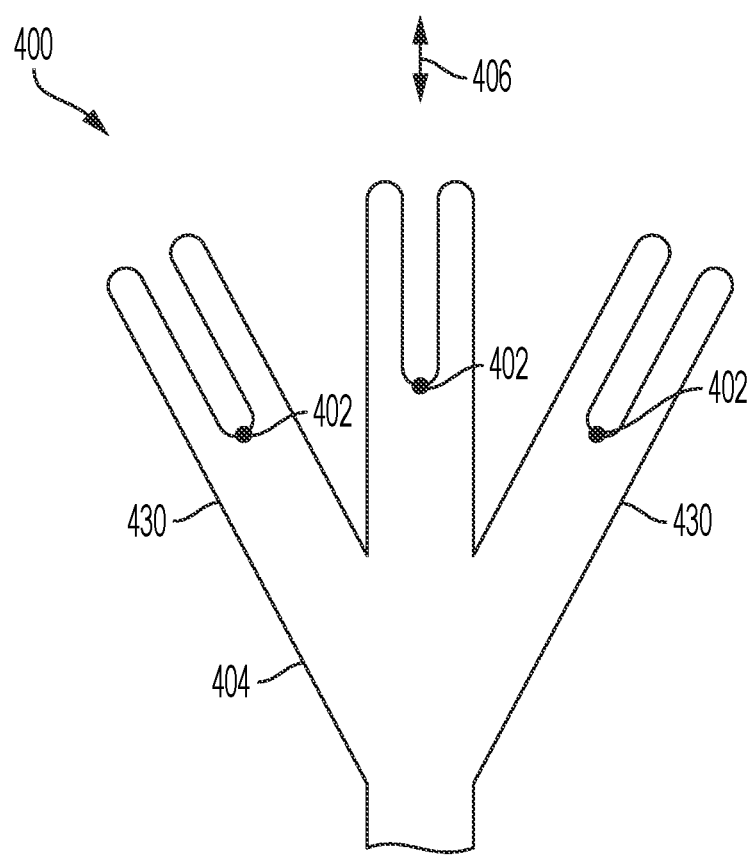
FIG. 7 is a schematic side view of an inflatable implantable tumor treating field apparatus as disclosed herein, wherein the apparatus comprises a plurality of inflatable portions.

Referring to FIG. 7, in some aspects, at least a portion 430 of the inflatable body 404 can be configured to extend radially outward with respect to the longitudinal axis 406 upon inflation of the inflatable body. Optionally, a plurality of portions 430 of the inflatable body 404 can be configured to extend radially outward with respect to the longitudinal axis 406 of the inflatable body 404. Optionally, at least one stimulation zone 402 can be positioned on each of the portions 430 of the body that is configured to extend radially outward. Optionally, each of the portions 430 of the body can be independently inflatable via separate valves or conduits, with each portion 430 being fluidly isolated from other radially extending portions 430. In some optional aspects, and as shown in FIG. 7, it is contemplated that the radially extending portions 430 can have a diameter and/or length that is substantially the same as the diameter and/or length of a portion of the inflatable body 404 that extends along the longitudinal axis 406. In other aspects, it is contemplated that the radially extending portions 430 can have a diameter and/or length that is greater than or less than the diameter and/or length of a portion of the inflatable body 404 that extends along the longitudinal axis 406. In these aspects, it is contemplated that the diameters and/or lengths can differ by at least 10%, by at least 15%, by at least 20%, by at least 25%, by at least 40%, by at least 50%, or by at least 75%.

By eliminating the need for applying a pushing force (or other mechanical force) to the proximal end of an implanted apparatus to position stimulation zones at a target site, it is contemplated that inflation of the body 404 can minimize damage to tissue as the stimulation zones are positioned at the target site.

Figure 8A:
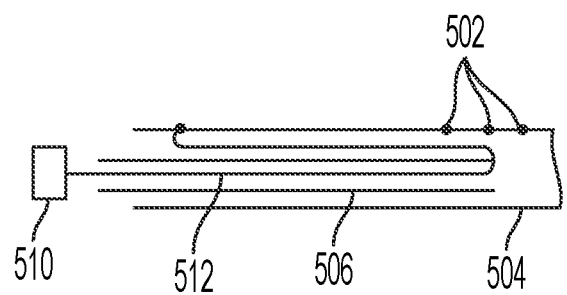
FIG. 8A is a schematic cross sectional view of an implantable telescoping treating field apparatus as disclosed herein, wherein the apparatus is in a compact configuration.
Figure 8B:
FIG. 8B a schematic cross sectional view of the implantable telescoping treating field apparatus as in FIG. 8A wherein the apparatus is in an extended configuration.

Referring to FIGS. 8A and 8B, a telescopic implantable TTField apparatus 500 can comprise a first body 504 that is telescopically coupled to a second body 506 so that the first body 506 is slidable with respect to the second body 506 along a longitudinal axis 508. Optionally, the first and second bodies 504, 506 can comprise metallic material. For example, an actuator 510 can be configured to slide the first body 504 with respect to the second body 506. For example, the actuator 510 can comprise a cable 512 that extends through the second body, over a distal end of the second body, and couples to the first body 504 so that retraction of the cable 512 (in a proximal direction) causes distal movement of the first body (see FIG. 8B). Optionally, the actuator 510 can comprise a plurality of such cables 512. Alternatively, it is contemplated that the actuator 510 can comprise: a threaded shaft that extends through the second body 506 and is coupled to the first body 504; and a rotation knob (or other accessible structure) that is rotationally and/or threadedly coupled to the threaded shaft such that rotation of the rotation knob effects a corresponding axial movement of the first body 504. As another alternative, it contemplated that the actuator 510 can comprise at least one elongate shaft with an external/accessible portion that extends through the second body 506 and is coupled to the first body 504 such that axial advancement or retraction of the elongate shaft causes a corresponding advancement or retraction of the first body 504. Additionally, or alternatively, in various optional aspects, it is contemplated that the actuator 510 can comprise a laparoscopic manipulator that is configured to provide three-dimensional (X-, Y-, and Z-axis control) of devices during a surgical procedure as is known in the art. Although specific examples of the actuator 510 are disclosed herein, it is contemplated that any suitable mechanism for effecting relative axial movement between the first and second bodies can be used.

A plurality of stimulation zones 502 can be disposed along the first body 504. Optionally, the stimulation zones 502 can be portions of the first body. In further aspects, for example, the stimulation zones can be electrodes that are coupled to individual electrical leads that extend through an interior of the first and second bodies 504, 506.

Figure 9:
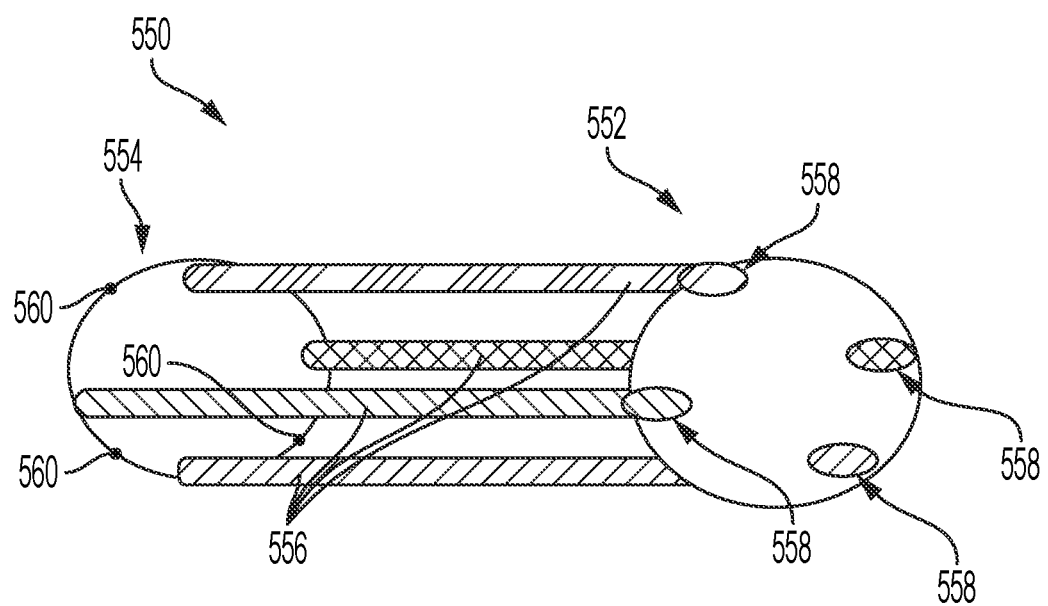
FIG. 9 is a schematic of an inflatable implantable tumor treating field apparatus as disclosed herein, wherein the apparatus comprises a plurality of independently inflatable bodies for controlling its direction of elongation.

Referring to FIG. 9, in some aspects, an implantable TTField apparatus 550 can have a proximal end 552 and a distal end 554 that are spaced by a length. A plurality of inflatable bodies 556 (e.g., two bodies, three bodies, four bodies, or more) can extend between the proximal end 552 and the distal end 554. Optionally, in exemplary aspects, the inflatable bodies 556 can be configured for significant axial expansion but only limited radial expansion; optionally, the inflatable bodies 556 can have a maximum inflated diameter that avoids contact with other inflatable bodies. However, embodiments in which a limited amount of contact between inflatable bodies is present are also contemplated. Optionally, the proximal end 552 and the distal end 554 can comprise respective support portions (e.g., circular support portions) that are coupled to the inflatable bodies 556 and formed of flexible material. The inflatable bodies 556 can have respective inflation inputs 558 (e.g., inflation ports) at the proximal end 552. By selectively inflating one or more of the bodies 556 (optionally, inflating multiple bodies simultaneously) through their corresponding inflation inputs 558, the distal end 554 can be extended away from the proximal end 552 in a select direction. For example, inflating all bodies simultaneously can cause the distal end to extend away from the proximal end in an axial direction. If all bodies are substantially equally inflated, then the axial direction in which the distal end extends can be a distal or generally distal direction. If a selected body or group of adjacent bodies are more inflated than the remaining bodies, then it is contemplated that the selected body or group of adjacent bodies can dictate the axial direction in which the apparatus extends. For example, in an embodiment having four bodies as shown in FIG. 9, inflating two adjacent bodies on a first transverse side of the TTField apparatus 550 can cause the distal end 554 to extend away from the proximal end 552 in an axial direction moving away from the first transverse side of the TTField apparatus 550. More particularly, the portions of the two adjacent bodies that extend axially beyond the distal ends of the other bodies are drawn toward the other bodies due to the support portion positioned at the distal ends of the inflatable bodies. A plurality of stimulation zones 560 can be positioned at the distal end and/or along the length of the TTField apparatus 550. Optionally, at least one stimulation zone 560 can be defined by or coupled to a respective inflatable body 556. Optionally, the plurality of stimulation zones can comprise at least two stimulation zones that are fixedly secured to or defined by a frame portion at the distal end. In exemplary aspects, it is contemplated that a plurality of fluid (e.g., pressurized air) conduits can be in fluid communication with the respective inflation inputs to permit selective inflation of respective bodies 556. It is contemplated that a source of air or other fluid can be selectively operated by a clinician to control inflation of the bodies 556. It is further contemplated that controlled decoupling of the fluid conduits, application of negative pressure, and/or release valves can be used to permit selective deflation of the bodies 556. In exemplary aspects, it is contemplated that the fluid conduits and TTField apparatus 550 can be advanced or retracted within the body of a patient as a unitary structure using conventional techniques.

Figure 10A:
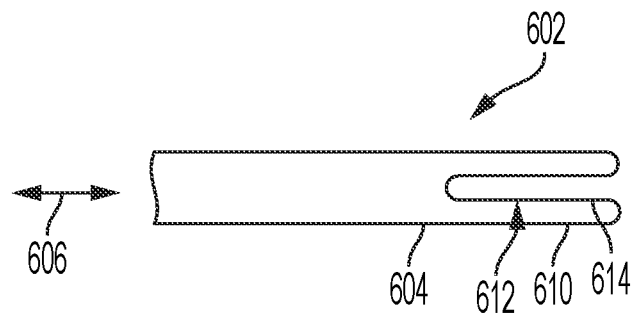
FIG. 10A is a schematic of a body of an inflatable implantable tumor treating field system, wherein the body is in a compact configuration.
Figure 10B:
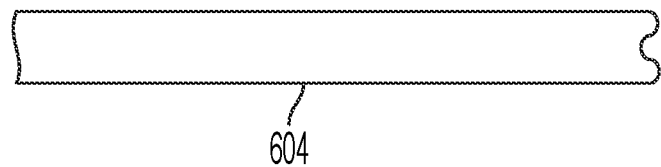
FIG. 10B is a schematic of the body of the inflatable implantable tumor treating field system, wherein the body is in an inflated configuration.
Figure 10C:
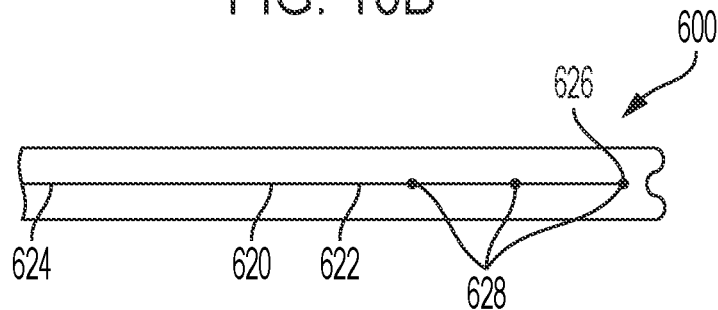
FIG. 10C is a schematic of the inflatable implantable tumor treating field system having an electric field-generating assembly within the inflated body.

Referring to FIGS. 10A-10C, a system 600 can comprise a guide 602 comprising an inflatable body 604 having a longitudinal axis 606. The inflatable body 604 of the guide 602 can optionally have at least one flexible wall 608 that is configured to expand along the longitudinal axis 606. In further aspects, the inflatable body can comprise a first portion 610 (e.g., a proximal portion) defining an interior 612 and a second portion 614 (e.g., a distal portion) that, before inflation, can be folded within the interior of the first portion of the body (e.g., in a proximal direction). Optionally, after inflation, the first and second portions of the inflatable body can cooperate to define a length 616 of the inflatable body 602 along the longitudinal axis 606. In some optional aspects, the guide 602 can comprise a bioresorbable material. Accordingly, after use, the guide 602 can remain in the body of the patient. It is contemplated that the guide can be configured further as described with reference to the body 404 in FIGS. 4A-6B.

An electric field-generating assembly 620 can be configured for receipt within the inflatable body 604 of the guide 602. The electric field-generating assembly 620 can comprise a cable 622 having a length between a proximal end 624 and a distal end 626. In some aspects, the cable 622 can be sufficiently rigid so that pushing on the proximal end 624 of the cable 622 can move the distal end 626 distally into the guide. The interior walls of the inflatable body can guide the electric field-generating assembly 620 toward the distal end of the guide. The electric field-generating assembly 620 can further comprise a plurality of stimulation zones 628. Optionally, the electric field generating assembly 620 can comprise a cable having a plurality of leads, with each lead extending to a respective stimulation zone.

Positioning the Stimulation Zones

Figure 12:
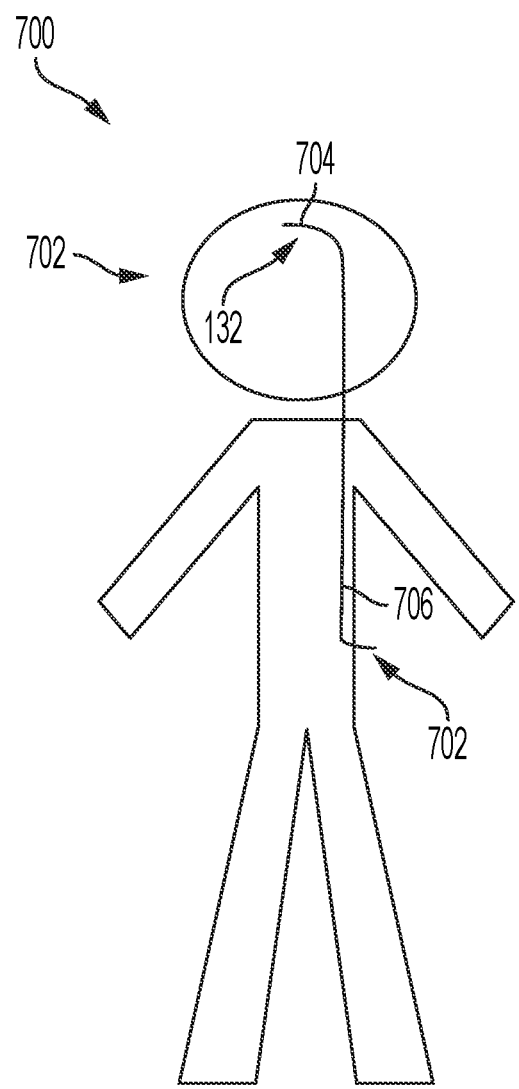
FIG. 12 is a schematic of a patient, showing positioning of the implantable apparatuses and systems as disclosed herein.

Referring to FIG. 12, the stimulation apparatuses and systems disclosed herein can be positioned proximate to a target site (e.g., a tumor 132, FIG. 1A). For example, for glioblastoma, at least a portion of the implantable TTField apparatus can be positioned in the subdural space. It is contemplated that the stimulation zones can be positioned to generally surround the tumor. In this way, fields emitted therefrom can pass through the tumor. In further aspects, at least one of the stimulation zones can be positioned within or in contact with the tumor. It is further contemplated that the stimulation zones can be positioned so that electric fields traveling between a first pair of stimulation zones can be perpendicular or substantially perpendicular to electric fields traveling between a second pair of stimulation zones. In exemplary aspects, it is contemplated that the intensities of electric fields can be mapped in the target site to determine an optimal placement of the stimulation zones. For example, it is contemplated that Applicant's NOVOTAL system can be used to identify optimal locations for the stimulation zones. As another example, it is contemplated that optimal locations for placement of the stimulation zones can be determined in accordance with the methods disclosed in U.S. Provisional Patent Application No. 63/002,937, entitled "Methods, Systems, and Apparatuses for Assisted Array Placement," which is incorporated herein by reference in its entirety. More particularly, such methods can comprise determining a transducer array map, determining image data associated with a portion of a subject's body, registering the image data to a three-dimensional (3D) model of the portion of the subject's body, wherein the 3D model comprises one or more positions indicated by the transducer array map, and generating composite data comprising the image data and one or more representations of transducer arrays associated with the one or more positions indicated by the transducer array map. In other aspects, such methods can comprise determining a three-dimensional (3D) model of a portion of the subject's body, determining, based on the 3D model, a transducer array map, wherein the transducer array map indicates one or more positions on the 3D model, receiving an image of the portion of the subject's body, determining that the image corresponds to the 3D model, and generating, based on determining that the image corresponds to the 3D model, a composite image comprising the image, the 3D model, and one or more images of transducer arrays associated with the one or more positions.

The stimulation apparatuses and systems disclosed herein can be inserted into the body of the patient 700 from an insertion site 702. In some optional aspects, it is contemplated that the insertion site can be in the patient's abdomen. In this way, the stimulation apparatus can be less conspicuous and intrusive into the patient's daily life (in comparison to devices implanted near prominent locations on the body). Accordingly, at least a first portion 704 of the apparatus can be disposed at the target site, and another portion 706 of the apparatus can extend to the insertion site. In further aspects, the stimulation apparatus can be inserted into the patient's head or body proximate to the target site.

In some aspects, the disclosed apparatuses can be inserted within the body of the patient using a catheter. However, in some aspects, when a bladder is used as disclosed herein, it is contemplated that the apparatuses can be implanted without the use of a catheter.

In order to determine proper placement, various types of imaging can be used. For example, in some aspects, X-ray imaging can detect the position of the implantable TTField apparatus. In further aspects, various imaging devices can detect conductive material in the apparatus. In still further aspects, radiographic material or other tracking marker(s) can be incorporated into the apparatus (e.g., at the distal end) for detecting its position within the body of the patient. In further aspects, the apparatus can be configured to emit an electric field that can optionally be different from the tumor-treating fields, and the emitted electric fields can be detected.

Once the stimulation zones have been positioned, the apparatus can be coupled to the electric field generator 12 (FIG. 11) and can be used to provide TTFields to the target site.

To permit removal of the TTField apparatus, the elongate elements can be retracted. Optionally, the elongate elements can be retracted via an actuator. Additionally, or alternatively, it is contemplated that movement of the TTField apparatus in a direction away from the patient can cause deployed elongate elements (e.g., fingers) to retract or close.

Positioning of Stimulation Zones for Specific Embodiments

Referring to FIGS. 1A and 1B, at least a portion (or, optionally, an entirety) of the implantable TTField apparatus 100 can be inserted in to a body of a patient until a select portion of the apparatus reaches a target site. Once implanted in a desired position, the plurality of elongate elements can be deployed into the deployed position at the target site. For example, the actuator 116 can be actuated to spread the plurality of elongate elements. After use, the actuator can optionally retract the plurality of elongate elements back to the retracted position.

Referring to FIGS. 2A-2C, at least a portion (or, optionally, an entirety) of the implantable TTField apparatus 200 can be inserted in to a body of a patient until a select portion of the apparatus is in proximity to the target site. Once implanted in a desired position, the bladder 204 can be inflated to deploy the plurality of stimulation zones into desired locations relative to the target site.

Referring to FIG. 3, at least a portion (or, optionally, an entirety) of the implantable TTField apparatus 250 can be inserted in to a body of a patient until a select portion of the apparatus is in proximity to the target site. Once implanted in a desired position, the bladders 254 can be inflated to deploy the plurality of stimulation zones into desired locations relative to the target site.

Referring to FIGS. 4A-7, at least a portion (or, optionally, an entirety) of the implantable TTField apparatus 400 can be inserted into the patient. The body 412 can be inflated to position the plurality of conductive zones at desired locations relative to the target site. For example, a gel (e.g., a conductive epoxy or other conductive gel), can be injected into an inlet of the body. In exemplary aspects, the inflatable body can be inserted into the patient using a catheter that guides the inflatable body into a selected position and/or orientation prior to inflation.

Referring to FIG. 8, the apparatus 500 can be at least partially (or, optionally, entirely) inserted into the body of the patient. The actuator can be actuated to extend the first body with respect to the second body until the stimulation zones are positioned in a desired location with respect to the target site.

Referring to FIG. 9, the apparatus 550 can be at least partially (or, optionally, entirely) inserted into the body of the patient. Some or all of the inflatable bodies can be inflated (e.g., injecting a biocompatible gel) until the distal end the stimulation zones are positioned in a desired location with respect to the target site. For example, some or all of the inflatable bodies can be incrementally inflated (e.g., all four bodies can be inflated to move the distal end a first distance, then two adjacent bodies can be inflated to move the distal end transversely, then all four bodies can be inflated, etc.) until the desired position of the distal end within the patient is reached.

Referring to FIGS. 10A-10C, at least a portion of the guide can be inserted into the body of the patient. The body of the guide can be inflated until a distal portion of the body reaches a desired position in the body of the patient. The electric field generating assembly can then be inserted into the guide until the stimulation zones are positioned in a desired location with respect to the target site.

Exemplary Materials

In exemplary aspects, the bladders disclosed herein can comprise one or more of the following materials: silicone, PET, polyvinyl chloride, polypropylene, polyethylene, polyurethanes, polyamides, polyesters, latex, natural rubber, synthetic rubber, polyether block amides, and elastomers, mixtures, or copolymers thereof. In some aspects, the bladders can comprise multiple layers, each layer comprising one or more of the aforementioned materials.

In exemplary aspects, the stimulation zones disclosed herein can be covered or made with an antimicrobial or hygienic promoting coating such as pMTAC or pDA-g-pMTAC combo, silver, tin, copper, ZnO/Ti spray, DMDC-Q-g-EM hydrogel, platinum, titanium, alloys, stainless steel, cobalt or cobalt-based alloys, cobalt chromium, magnesium alloys, or other material that is biocompatible.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An apparatus for generating an electric field, the apparatus comprising: a plurality of elongate elements, the plurality of elongate elements comprising at least a first elongate element and a second elongate element, wherein each elongate element of the plurality of elongate elements has: a proximal end; an opposed distal end; and at least one stimulation zone; wherein the plurality of elongate elements are coupled together at their respective proximal ends, wherein the plurality of elongate elements are selectively moveable about and between a retracted position and a deployed position, wherein, in the retracted position, the respective distal ends of the first and second elongate elements are spaced by a first distance, wherein, in the deployed position, the respective distal ends of the first and second elongate elements are spaced by a second distance that is greater than the first distance.

Aspect 2: The apparatus of aspect 1, wherein each stimulation zone comprises an electrode.

Aspect 3: The apparatus of aspect 1 or aspect 2, further comprising an actuator that is configured to move the plurality of elongate elements from the retracted position to the deployed position.

Aspect 4: The apparatus of aspect 3, wherein the actuator is a mechanical actuator that is mechanically coupled to at least one of the first elongate element or the second elongate element.

Aspect 5: The apparatus of aspect 3 or aspect 4, wherein the first elongate element is mechanically coupled to the second elongate element.

Aspect 6: The apparatus of aspect 5, further comprising an actuation cable that mechanically couples the first elongate element to the second elongate element, wherein a tension applied to the actuation cable causes the plurality of elongate elements to deploy from the retracted position to the deployed position.

Aspect 7: The apparatus of any one of the preceding aspects, wherein the plurality of elongate elements comprises at least one intermediate element that is positioned between, and coupled to, the first and second elongate elements.

Aspect 8: The apparatus of any one of the preceding aspects, further comprising at least one cable comprising a plurality of electrical leads, wherein each electrical lead is in electrical communication with a respective stimulation zone of an elongate element of the plurality of elongate elements.

Aspect 9: The apparatus of any one of the preceding aspects, wherein at least one elongate element of the plurality of elongate elements comprises a plurality of stimulation zones.

Aspect 10: The apparatus of aspect 9, wherein each zone of the plurality of stimulation zones of the plurality of elongate elements is configured to be independently activated to provide electrical fields between itself and any other zone of the plurality of stimulation zones.

Aspect 11: An apparatus comprising: a bladder; and a plurality of stimulation zones coupled to the bladder, wherein the plurality of stimulation zones comprise a first stimulation zone and a second stimulation zone, wherein the plurality of stimulation zones are configured to generate an electric field, wherein inflation of the bladder causes the plurality of stimulation zones to deploy from a retracted configuration to a deployed configuration, wherein, when the plurality of stimulation zones are in the retracted configuration, the first and second stimulation zones are spaced by a first distance, wherein, when the plurality of stimulation zones are in the deployed configuration, the first and second stimulation zones are spaced by a second distance that is greater than the first distance.

Aspect 12: The apparatus of aspect 11, further comprising a frame coupled to the bladder, wherein the frame is configured to determine a shape of the bladder when the bladder is inflated.

Aspect 13: The apparatus of aspect 11 or aspect 12, further comprising a plurality of elongate elements coupled to the bladder, wherein the plurality of elongate elements comprises at least a first elongate element and a second elongate element, wherein each elongate element of the plurality of elongate elements has: a proximal end; an opposed distal end; and at least one stimulation zone of the plurality of stimulation zones, wherein the plurality of elongate elements are coupled together at their respective proximal ends, wherein the plurality of elongate elements are selectively moveable about and between a retracted position and a deployed position, wherein, in the retracted position, the respective distal ends of the first and second elongate elements are spaced by a third distance, wherein, in the deployed position, the respective distal ends of the first and second elongate elements are spaced by a fourth distance that is greater than the third distance.

Aspect 14: The apparatus of aspect 13, wherein the plurality of elongate elements are disposed within the bladder.

Aspect 15: An apparatus comprising: an inflatable body having a longitudinal axis; and a plurality of stimulation zones coupled to the inflatable body, wherein the stimulation zones are configured to produce an electric field, and wherein inflation of the body causes elongation of the body along the longitudinal axis.

Aspect 16: The apparatus of aspect 15, wherein the inflatable body comprises at least one flexible wall so that a sufficient pressure within the body causes the at least one flexible wall to expand along the longitudinal axis to increase a longitudinal length of the inflatable body.

Aspect 17: The apparatus of aspect 15, wherein, prior to inflation the inflatable body, a first portion of the body defines an interior, and a second portion of the body is folded within the interior of the first portion of the body.

Aspect 18: The apparatus of aspect 17, wherein, after inflation, the first and second portions of the body cooperate to define a length of the inflatable body along the longitudinal axis.

Aspect 19: The apparatus of aspect 15, wherein the plurality of stimulation zones comprises a first stimulation zone and a second stimulation zone, wherein, prior to inflation of the inflatable body, the first stimulation zone is spaced from the second stimulation zone by a first distance, wherein, upon inflation of the inflatable body, the first stimulation zone is spaced from the second stimulation zone by a second distance, wherein the second distance is greater than the first distance.

Aspect 20: The apparatus of aspect 15, wherein, the plurality of stimulation zones comprises a first stimulation zone and a second stimulation zone, wherein, prior to inflation of the inflatable body, the first stimulation zone is spaced from the second stimulation zone by a first distance, wherein, upon inflation of the inflatable body, the first stimulation zone remains spaced from the second stimulation zone by the first distance.

Aspect 21: The apparatus of aspect 15, wherein the inflatable body comprises at least one portion that is configured to extend radially outwardly with respect to the longitudinal axis upon inflation of the inflatable body, wherein at least one stimulation zone of the plurality of stimulation zones is positioned on the at least one portion that is configured to extend radially outwardly.

Aspect 22: The apparatus of aspect 21, wherein the at least one portion that is configured to extend radially outwardly with respect to the longitudinal dimension comprises a plurality of portions that are configured to extend radially outwardly with respect to the longitudinal axis upon inflation of the inflatable body.

Aspect 23: An apparatus having a longitudinal axis and comprising: a first body that is telescopically coupled to a second body so that the first body is slidable with respect to the second body along the longitudinal axis; a plurality of stimulation zones disposed along the first body, wherein the stimulation zones are configured to produce an electric field; and an actuator that is configured to slide the first body with respect to the second body.

Aspect 24: A system comprising: a guide comprising an inflatable body having a longitudinal axis; an electric field-generating assembly configured for receipt within the inflatable body and comprising: a cable having a length; and a plurality of stimulation zones disposed along the length of the cable, wherein the plurality of stimulation zones are configured to produce an electric field.

Aspect 25: The system of aspect 24, wherein the inflatable body comprises at least one flexible wall so that a sufficient pressure within the inflatable body causes the at least one flexible wall to expand along the longitudinal axis to increase a longitudinal length of the inflatable body.

Aspect 26: The system of aspect 24, wherein, prior to inflation the inflatable body, a first portion of the body defines an interior, and a second portion of the inflatable body is folded within the interior of the first portion of the body.

Aspect 27: The system of aspect 24, wherein, after inflation, the first and second portions of the inflatable body cooperate to define a length of the inflatable body along the longitudinal axis.

Aspect 28: The system of aspect 24, wherein the guide comprises a bioresorbable material.

Aspect 29: A method comprising: inserting at least a portion of the apparatus as in any one of aspects 1-10 into a body of a patient until a select portion of the apparatus reaches a target site; and deploying the plurality of elongate elements into the deployed configuration at the target site.

Aspect 30: The method of aspect 29 wherein inserting the at least a portion of the apparatus comprises inserting the at least a portion of the apparatus in a patient at an insertion site that is at the patient's abdomen so that the plurality of elongate elements of the apparatus are disposed at the target site and a second portion of the apparatus extends to the insertion site.

Aspect 31: The method of aspect 29 or aspect 30, further comprising delivering current through the plurality of stimulation zones to generate an electric field at the target site.

Aspect 32: A method comprising: inserting at least a portion of an apparatus as in any one of aspects 11-14 into a body of a patient until the plurality of stimulation zones of the apparatus are in proximity to a target site; and inflating the bladder to deploy the plurality of stimulation zones into desired locations relative to the target site.

Aspect 33: The method of aspect 32, further comprising delivering current through the plurality of stimulation zones to generate an electric field at the target site.

Aspect 34: A method comprising: inserting at least a portion of an apparatus as in any one of aspects 15-22 into a body of a patient until the plurality of stimulation zones of the apparatus are in proximity to a target site; and inflating the body to deploy the plurality of stimulation zones into the deployed configuration at desired locations relative to the target site.

Aspect 35: The method of aspect 34, further comprising delivering current through the plurality of stimulation zones to generate an electric field at the target site.

Aspect 36: A method of using the system as in any one of aspects 24-28, the method comprising: inserting the guide into a body of a patient; inflating the body of the guide until the body reaches a desired position in the body of the patient; and inserting the electric field-generating assembly into the guide until the stimulation zones of the electric field-generating assembly are positioned at a desired location with respect to a target site in the body of the patient.

Aspect 37: The method of aspect 36, wherein inflating the body comprises injecting a conductive gel into the body.

Although the foregoing invention has been described in some detail by way of illustration and example for purposes of clarity of understanding, certain changes and modifications may be practiced within the scope of the appended claims.

What is claimed is:

1. An apparatus for generating an electric field to treat a tumor, the apparatus comprising:
an electrical signal generator; and
a plurality of elongate elements, the plurality of elongate elements comprising at least a first elongate element and a second elongate element, wherein each elongate element of the plurality of elongate elements has:
a proximal end;
an opposed distal end; and
at least one stimulation zone,
wherein the plurality of elongate elements are coupled together at their respective proximal ends, wherein the plurality of elongate elements are selectively moveable about and between a retracted position and a deployed position,
wherein, in the retracted position, the respective distal ends of the first and second elongate elements are spaced by a first distance,
wherein, in the deployed position, the respective distal ends of the first and second elongate elements are spaced by a second distance that is greater than the first distance, wherein the electrical signal generator is electrically coupled to the at least one stimulation zone of each elongate element of the plurality of elongate elements, and wherein, when the plurality of elongate elements are in the deployed position, the electrical signal generator is configured to generate an alternating voltage waveform at at least one frequency in a range from 50 kHz to 500 kHz to thereby generate tumor treating fields having an intensity from about 0.1 V/cm to about 10 V/cm between the at least one stimulation zone of at least two elongate elements of the plurality of elongate elements.

2. The apparatus of claim 1, wherein each stimulation zone comprises an electrode.

3. The apparatus of claim 1, further comprising an actuator that is configured to move the plurality of elongate elements from the retracted position to the deployed position.

4. The apparatus of claim 3, wherein the actuator is a mechanical actuator that is mechanically coupled to at least one of the first elongate element or the second elongate element.

5. The apparatus of claim 3, wherein the first elongate element is mechanically coupled to the second elongate element.

6. The apparatus of claim 5, further comprising an actuation cable that mechanically couples the first elongate element to the second elongate element, wherein a tension applied to the actuation cable causes the plurality of elongate elements to deploy from the retracted position to the deployed position.

7. The apparatus of claim 1, wherein the plurality of elongate elements comprises at least one intermediate element that is positioned between, and coupled to, the first and second elongate elements.

8. The apparatus of claim 1, further comprising at least one cable comprising a plurality of electrical leads, wherein each electrical lead is in electrical communication with a respective stimulation zone of an elongate element of the plurality of elongate elements.

9. The apparatus of claim 1, wherein at least one elongate element of the plurality of elongate elements comprises a plurality of stimulation zones.

10. The apparatus of claim 9, wherein each zone of the plurality of stimulation zones of the plurality of elongate elements is configured to be independently activated to provide electrical fields between itself and any other zone of the plurality of stimulation zones.

11. A method comprising:
inserting at least a portion of the apparatus as in claim 1 into a body of a patient until a select portion of the apparatus reaches a target site, wherein the target site is the tumor; and
deploying the plurality of elongate elements into the deployed configuration at the target site.

12. The method of claim 11 wherein inserting the at least a portion of the apparatus comprises inserting the at least a portion of the apparatus in a patient at an insertion site that is at the patient's abdomen so that the plurality of elongate elements of the apparatus are disposed at the target site and a second portion of the apparatus extends to the insertion site.

13. The method of claim 11, further comprising generating, by the electrical signal generator, alternating the voltage waveform to thereby generate the tumor treating fields between the at least one stimulation zone of the at least two elongate elements of the plurality of elongate elements having an intensity from about 0.1 V/cm to about 10 V/cm at the target site.

14. A method comprising:
inserting at least a portion of an apparatus as in claim 1 into a body of a patient until the at least one stimulation zone of each elongate element of the plurality of elongate elements of the apparatus are in proximity to a target site, wherein the target site is the tumor; and
moving the plurality of elongate elements to the deployed position to deploy each stimulation zone of the at least one stimulation zone of the plurality of elongate elements into desired locations relative to the target site.

15. The method of claim 14, further comprising generating, by the electrical signal generator, the alternating voltage waveform to thereby generate the tumor treating fields between the at least one stimulation zone of the at least two elongate elements of the plurality of elongate elements having an intensity from about 0.1 V/cm to about 10 V/cm at the target site.

16. The apparatus of claim 1, wherein the electrical signal generator is configured to generate the alternating voltage waveform at at least one frequency from 100 kHz to 300 kHz.

17. The apparatus of claim 1, further comprising a webbing or a support cable extending between adjacent elongate elements of the plurality of elongate elements.

18. The apparatus of claim 1, wherein each elongate element of the plurality of elongate elements is elongate along a length, wherein the at least one stimulation zone of a first elongate element of the plurality of elongate elements is elongate along the length of the first elongate element.

19. The apparatus of claim 1, wherein the at least one stimulation zone of a first elongate element of the plurality of elongate elements extends circumferentially around said first elongate element.

20. The apparatus of claim 1, wherein the at least two elements of the plurality of elongate elements, when in the deployed configuration, are configured to be positioned on opposite sides of the tumor.

* * * * *